(12) United States Patent
Ramesh

(10) Patent No.: US 9,732,011 B2
(45) Date of Patent: Aug. 15, 2017

(54) INTEGRATED PROCESS FOR THE PREPARATION OF OLEFINS

(71) Applicant: SHELL OIL COMPANY, Houston, TX (US)

(72) Inventor: Rajaram Ramesh, Zoetermeer (NL)

(73) Assignee: SHELL OIL COMPANY, Houston, TX (US)

( * ) Notice: Subject to any disclaimer, the term of this patent is extended or adjusted under 35 U.S.C. 154(b) by 54 days.

(21) Appl. No.: 14/412,697

(22) PCT Filed: Jul. 1, 2013

(86) PCT No.: PCT/EP2013/063839
§ 371 (c)(1),
(2) Date: Jan. 5, 2015

(87) PCT Pub. No.: WO2014/005998
PCT Pub. Date: Jan. 9, 2014

(65) Prior Publication Data
US 2015/0158783 A1    Jun. 11, 2015

(30) Foreign Application Priority Data

Jul. 5, 2012  (EP) ..................... 12175194

(51) Int. Cl.
*C07C 1/20*  (2006.01)
*C07C 7/08*  (2006.01)
(Continued)

(52) U.S. Cl.
CPC .................. *C07C 1/20* (2013.01); *C07C 4/04* (2013.01); *C07C 7/08* (2013.01); *C10G 3/49* (2013.01);
(Continued)

(58) Field of Classification Search
CPC .... C07C 1/20; C07C 1/22; C07C 4/04; C07C 7/08; C07C 11/04; C07C 11/06;
(Continued)

(56) References Cited

U.S. PATENT DOCUMENTS 3,365,387 A    1/1968  Cahn et al.
4,061,562 A    12/1977 McKinney et al.
(Continued)

FOREIGN PATENT DOCUMENTS

CN    101802138    8/2010
CN    102408294    11/2014
(Continued)

*Primary Examiner* — Sharon Pregler

(57) ABSTRACT

The present invention provides an integrated process for the preparation of olefins, which process comprises the steps of:
(a) reacting an oxygenate and/or olefinic feed in a reactor to form an effluent which comprises olefins;
(b) fractionating at least part of the effluent into two olefinic product fractions;
(c) subjecting a hydrocarbon feedstock in a reactor to a steam cracking process to form an effluent which comprises olefins including butadiene;
(d) combining at least part of the first olefinic product fraction as obtained in step (b) and at least part of the second effluent which comprises olefins as obtained in step (c) to form a combined olefinic product stream comprising at least ethylene, propylene and butadiene; and
(e) separating at least part of the combined olefinic product stream as obtained in step (d) to form a fraction comprising ethylene and/or propylene and a fraction that comprises butadiene.

12 Claims, 1 Drawing Sheet

(51) Int. Cl.
    *C10G 3/00*     (2006.01)
    *C10G 9/36*     (2006.01)
    *C07C 4/04*     (2006.01)

(52) U.S. Cl.
    CPC ............... *C10G 3/52* (2013.01); *C10G 9/36* (2013.01); *C07C 2529/40* (2013.01); *C10G 2300/1081* (2013.01); *C10G 2400/20* (2013.01); *C10G 2400/22* (2013.01); *Y02P 20/125* (2015.11); *Y02P 30/42* (2015.11)

(58) Field of Classification Search
    CPC ............ C07C 11/167; C07C 2529/40; C10G 2300/1081; C10G 2400/20; C10G 2400/22; C10G 3/49; C10G 3/52; C10G 9/36

See application file for complete search history.

(56) References Cited

U.S. PATENT DOCUMENTS

| | | |
|---|---|---|
| 8,178,060 B2 | 5/2012 | Corradi et al. |
| 2010/0206771 A1 | 8/2010 | Rothaemel et al. |
| 2010/0303691 A1 | 12/2010 | Corradi et al. |
| 2011/0112344 A1* | 5/2011 | Chewter ............ C01B 3/22 585/302 |
| 2012/0041243 A1 | 2/2012 | Senetar |
| 2012/0041244 A1 | 2/2012 | Montalbano et al. |

FOREIGN PATENT DOCUMENTS

| | | |
|---|---|---|
| CN | 102408296 | 1/2015 |
| WO | 2006020083 | 2/2006 |

\* cited by examiner

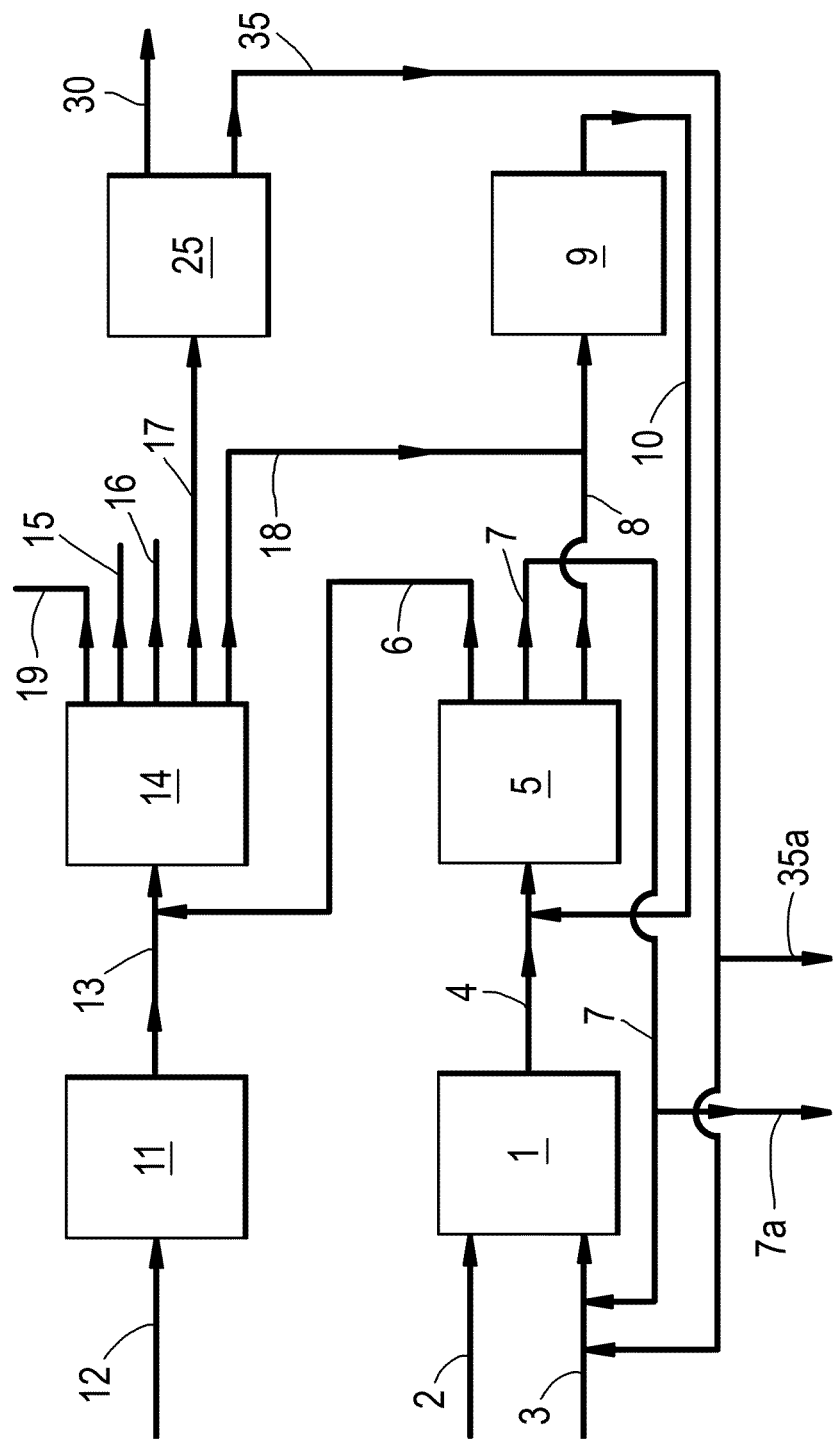

INTEGRATED PROCESS FOR THE PREPARATION OF OLEFINS

PRIORITY CLAIM

The present application is the National Stage (§371) of International Application No. PCT/EP2013/063839, filed Jul. 1, 2013, which claims priority from European Patent Application No. 12175194.5, filed Jul. 5, 2012, the disclosures of which are incorporated herein by reference.

FIELD OF THE INVENTION

The present invention relates to an integrated process for the preparation of olefins.

BACKGROUND OF THE INVENTION

There is an increasing demand for olefins in the chemical industry. In particular olefins such as ethylene, propylene, and butadiene are of commercial importance since they are used as building block chemicals for the preparation of petrochemicals and polymers. Ethylene and propylene are used for the production of polyethylene and polypropylene respectively, whereas butadiene is used for the production of polybutadiene and styrene-butadiene-rubber (SBR).

Processes for the preparation of olefins are known in the art. A major process for the preparation of olefins is the steam cracking of a paraffin-containing hydrocarbon feedstock such as naphtha, gas oil, ethane, propane and butane. Besides ethylene and propylene, these steam cracking processes also produce substantial amounts of butadiene, typically obtained as part of the C4 product fraction of the steam cracker product. The butadiene is retrieved from the C4 product fraction by extraction.

In recent years, other processes for the preparation of olefins have been developed, including oxygenate-to-olefins (OTO) processes. These processes typically produce more propylene than the earlier mentioned steam cracking processes and are therefore seen as a suitable means to provide a uniform product slate, i.e. comprising significant amounts of both ethylene and propylene.

In US 2010/0206771 A1, an integrated process for producing hydrocarbons, in particular $C_2$-$C_4$ has been described, using a combined plant with a steam cracker and a methanol-to-propylene (MTP) process, wherein the respective intermediate product streams of the steam cracker and the MTP are combined completely.

A disadvantage of the process of US 2010/0206771 is that the MTP product stream does not contain butadiene, as can be seen from Table 1 of US 2010/0206771. Consequently, the butadiene content in the steam cracker product stream is diluted by combining the steam cracker product stream with the MTP product stream. The efficiency of the butadiene extraction from the product is dependent on the butadiene concentration, whereby the efficiency of extraction decreases with decreasing butadiene concentration. As a result of the dilution of the butadiene concentration, less butadiene is extracted. Moreover, as part of the C4 product fraction is recycled to either the steam cracker or the MTP process, the remaining butadiene in the C4 product fraction is hydrogenated and thus must be considered lost. At the same time hydrogen and sufficient hydrogenation means must be provided to hydrogenate the residual butadiene.

Such a process leaves room for improvement in terms of butadiene recovery and hydrogen consumption.

Object of the present invention is to provide an integrated process of a steam cracker process and an OTO process for producing olefins in which the overall butadiene yield is improved.

SUMMARY OF THE INVENTION

It has now been found that this can be established when the various product streams are integrated in a particular manner.

Accordingly, the present invention relates to an integrated process for the preparation of olefins, which process comprises the steps of:

(a) reacting an oxygenate feed in a first reactor in the presence of a molecular sieve catalyst to form a first effluent which comprises olefins;

(b) fractionating at least part of the first effluent into a first olefinic product fraction comprising at least ethylene and propylene and a second olefinic product fraction which comprises olefins containing 4 or more carbon atoms;

(c) subjecting a paraffin-containing hydrocarbon feedstock in a second reactor to a steam cracking process to form a second effluent which comprises olefins, including butadiene;

(d) combining at least part of the first olefinic product fraction as obtained in step (b) and at least part of the second effluent which comprises olefins as obtained in step (c) to form a combined olefinic product stream comprising at least ethylene, propylene and a C4 hydrocarbon fraction comprising butadiene; and (e) subjecting at least part of the combined olefinic product stream as obtained in step (d) to one or more product separation treatments to form at least a product fraction which comprises ethylene and/or propylene and a C4 hydrocarbon product fraction that comprises butadiene.

The process according to the present invention allows for the integration of a steam cracking process and an OTO process, while preventing the undesired dilution of the butadiene in the combined effluent. As a consequence, a more efficient extraction of butadiene can be achieved, while less hydrogen is required to hydrogenate residual butadiene in the C4 hydrocarbon fraction.

BRIEF DESCRIPTION OF THE DRAWINGS

FIG. 1 provides a schematic representation of a process according to the invention.

DETAILED DESCRIPTION OF THE INVENTION

In step (a) of the present process an oxygenate feed is reacted in a first reactor in the presence of a molecular sieve catalyst to form a first effluent which comprises olefins.

In step (a), preferably oxygenates are converted into olefins.

The reactor to be used in step (a) can be an OTO reaction zone wherein the oxygenate feed is contacted with an oxygenate conversion catalyst under oxygenate conversion conditions, to obtain the first effluent comprising lower olefins. Reference herein to an oxygenate feed is to an oxygenate-comprising feed. In the OTO reaction zone, at least part of the feed is converted into a product containing one or more olefins, preferably including lower olefins, in particular ethylene and typically propylene.

The oxygenate used in the process according to the invention is preferably an oxygenate which comprises at least one oxygen-bonded alkyl group. The alkyl group preferably is a $C_1$-$C_5$ alkyl group, more preferably $C_1$-$C_4$ alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate feed include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof. More preferably, the oxygenate comprises methanol or dimethylether.

Preferably the oxygenate feed comprises at least 50 wt % of oxygenate, in particular methanol and/or dimethylether, based on total hydrocarbons, more preferably at least 70 wt %. Reference herein to hydrocarbons is to hydrocarbons including oxygenates The oxygenate feed can comprise an amount of diluent, such as nitrogen and water, preferably in the form of steam. In one embodiment, the molar ratio of oxygenate to diluent is between 10:1 and 1:10, preferably between 4:1 and 1:2, in particular when the oxygenate is methanol and the diluent is water (steam).

A variety of OTO processes is known for converting oxygenates such as for instance methanol or dimethylether to an olefin-containing product, as already referred to above. One such process is described in WO-A 2006/020083.

The molecular sieve catalyst to be used in step (a) suitably comprises one or more zeolite catalysts and/or one or more SAPO catalysts, such as SAPO-34. Molecular sieve catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

The molecular sieve catalyst preferably comprises a zeolite molecular sieve, also referred to as zeolites. More, preferably the molecular sieve catalysts comprise zeolites having 8-, 10- and/or 12-ring structures and an average pore size in the range of from about 3 Å to 15 Å.

Preferably, the amount of molecular sieve, preferably zeolite, is in the range of from 20 to 50 wt %, preferably of from 35 to 45 wt %, based on total weight of the molecular sieve catalyst composition.

Suitable zeolites include those of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Preferred zeolites comprise a more-dimensional zeolites, in particular of the MFI type, more in particular ZSM-5, or of the MEL type, such as zeolite ZSM-11. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a Silica-to-Alumina ratio (SAR) of at least 60, preferably at least 80. More preferably, the MFI-type zeolite has a Silica-to-Alumina ratio (SAR) in the range of from 60 to 150, more preferably of from 80 to 100.

Particular catalysts include catalysts comprising one or more zeolite having one-dimensional 10-membered ring channels, i.e. one-dimensional 10-membered ring channels, which are not intersected by other channels.

In one embodiment of the present invention use is made of a molecular sieve catalyst which comprises ZSM-5 and/or ZSM-11.

Preferred examples are zeolites of the MTT and/or TON type.

Preferably, the catalyst comprises at least 40 wt %, preferably at least 50% wt of such zeolites based on total zeolites in the catalyst.

In a particularly preferred embodiment the molecular sieve catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The present molecular sieve catalyst may comprise phosphorus as such (elemental phosphorus) or in a compound, i.e. phosphorous other than any phosphorus included in the framework of the molecular sieve. It is preferred that an MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the present molecular sieve catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolites having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that the molecular sieves in the hydrogen form are, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve catalyst used is in the hydrogen form. It is well known in the art how to produce such molecular sieve catalysts in the hydrogen form.

The molecular sieve catalyst particles can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. Spherical particles are normally obtained by spray drying. Preferably the average particle size is in the range of 1-500 μm, preferably 50-100 μm.

Preferably, the zeolite comprises a zeolite having 10-membered ring channels. Preferred zeolites include zeolites of the MTT-type, the TON-type, the MFI-type or the MEL-type.

The reaction conditions of the oxygenate conversion in step (a) include a reaction temperature of 350 to 1000° C., suitably from 350 to 750° C., preferably from 450 to 750° C., more preferably from 450 to 700° C., even more preferably 500 to 650° C.; and a pressure suitably from 1 bara to 50 bara, preferably from 1-15 bara, more preferably from 1-4 bara, even more preferably from 1.1-3 bara, and most preferably in from 1.3-2 bara.

Suitably, the oxygenate-comprising feed is preheated to a temperature in the range of from 120 to 550° C., preferably 250 to 500° C. prior to introducing it into the reactor in step (a).

Preferably, in addition to the oxygenate, an olefinic co-feed is provided along with and/or as part of the oxygenate feed. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species. The olefinic co-feed can also comprise propylene.

The reaction in step (a) may suitably be operated in a fluidized bed, e.g. a dense, turbulent or fast fluidized bed or a riser reactor or downward reactor system, and also in a fixed bed reactor, moving bed or a tubular reactor. A fluidized bed, e.g. a turbulent fluidized bed, fast fluidized bed or a riser reactor system are preferred.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to about 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the catalyst is fed at the top of the bed and travels through the bed in opposite direction with respect to the gas, whereby the catalyst leaves the vessel at the bottom. In a conventional riser reactor system the catalyst and the vapours will travel co-currently.

More preferably, a fluidized bed, in particular a turbulent fluidized bed system is used. Suitably, in such a moving bed reactor the oxygenate feed is contacted with the molecular sieve catalyst at a weight hourly space velocity of at least 1 hr$^{-1}$, suitably from 1 to 1000 hr$^{-1}$, preferably from 1 to 500 hr$^{-1}$, more preferably 1 to 250 hr$^{-1}$, even more preferably from 1 to 100 hr$^{-1}$, and most preferably from 1 to 50 hr$^{-1}$.

The first effluent as obtained in step (a) comprises advantageously at least 50 mol %, in particular at least 50 wt %, ethylene and propylene, based on total hydrocarbon content in the first effluent.

Suitably, the first effluent as obtained in step (a) comprises less than 6.0 wt % butadiene, preferably less than 5.0 wt %, based on the total weight of hydrocarbons containing 4 carbon atoms present in the first effluent.

In step (b) at least part of the first effluent is fractionated into a first olefinic product fraction comprising at least ethylene and propylene and a second olefinic product fraction which comprises olefins containing 4 or more carbon atoms.

Suitably, at least part of the second olefinic product fraction is recycled to step (a) as part of or all of the olefinic co-feed. If desired, at least part of the second olefinic product fraction can be withdrawn as product. In case, part of the second olefinic product fraction is recycled to step (a), it is preferred that at least a part of the second olefinic product fraction is withdrawn from the process as a purge stream to prevent the build up paraffins in the recycle to step (a). Preferably, in the range of 5 to 20 wt % of the second olefinic fraction is withdrawn as a purge stream.

At least a part of the second olefinic product fraction may also be provided to an olefin cracking process (OCP) reaction zone wherein the second olefinic product fraction, or part thereof, is contacted with an olefin conversion catalyst under olefin conversion conditions, to form a further effluent comprising lower olefins.

The second olefinic product fraction comprises C4+ olefins that will be converted to ethylene and/or propylene by contacting such a feed with the zeolite-comprising catalyst. Preferably, the second olefinic product fraction is contacted with the zeolite-comprising catalyst in step (a) at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, the second olefinic product fraction is provided to the OCP reaction zone together with a diluent. Examples of suitable diluents include, but are not limited to, such as water or steam, nitrogen, paraffins and methane. Under these conditions, at least part of the olefins in the second olefinic product fraction are converted to further ethylene and/or propylene.

Particular preferred molecular sieve catalysts for the OCP reaction are catalysts comprising at least one zeolite selected from MFI, MEL, TON and MTT type zeolites, more preferably at least one of ZSM-5, ZSM-11, ZSM-22 and ZSM-23 zeolites. In case the molecular sieve catalyst of step (a) is a zeolite catalyst it is preferred that the same catalyst is used in step (a) as well as in an optional step wherein the second olefinic product fraction is converted in an OCP reaction zone Also an OCP process may suitably be operated in a fluidized bed, e.g. a fast fluidized bed or a riser reactor or a downward reactor system, and also in a fixed bed reactor, moving bed or a tubular reactor. A fluidized bed, e.g. a fast fluidized bed or a riser reactor system are preferred.

Providing at least part of the second olefinic product fraction to an OCP reaction zone is of particular interest when the OTO reaction zone comprises molecular sieve catalyst that does not comprise a zeolite. In particular in case the molecular sieve catalyst comprises SAPO-34. Such catalysts are less suitable for converting olefinic co-feeds.

Suitably, at least part of the lighter olefins so formed is provided to step (b).

Preferably, step (b) includes separating the first effluent into a C3− fraction and a C4+ fraction. Step (b) is preferably carried out by passing the first effluent to separation section comprising at least a depropaniser unit and the first olefinic product fraction is retrieved as the top fraction of the depropaniser unit. The design of such separation section comprising at least a depropaniser unit is well known in the art and does not require any further explanation.

If desired, the second olefinic product fraction as obtained in step (b) can be fractionated to obtain at least a third olefinic product fraction comprising C4 olefins and a fourth olefinic product fraction comprising olefins having 5 or more carbon atoms. Suitably, at least part of the third olefinic product fraction so obtained is recycled to step (a). Preferably, part of third olefinic product fraction is withdrawn as a purge.

Suitably, at least part of the fourth olefinic product stream can be subjected to an olefin cracking process (OCP) to form lighter olefins. Preferably, the entire fourth olefinic product stream can be subjected to an olefin cracking process to form lighter olefins. In case the molecular sieve catalyst of step (a) is a zeolite catalyst it is preferred that the same catalyst is used in step (a) as well as in an optional step wherein the fourth olefinic product stream is converted in an OCP reaction zone Suitably, at least part of the lighter olefins so formed is provided to step (b). Preferably, the entire stream of lighter olefins so formed is provided to step (b).

In step (c), a paraffin-containing hydrocarbon feedstock is subjected in a second reactor to a steam cracking process to form a second effluent which comprises olefins including butadiene.

Steam cracking processes that can be applied in step (c) include known in the art. Suitable steam cracking processes to be used in step (c) are, for example, described in U.S. Pat. No. 3,365,387 and U.S. Pat. No. 4,061,562. In a steam cracking process the hydrocarbons are pyrolyzed in the presence of steam to form light olefins such as ethylene and propylene, and heavier products such as pyrolysis gas oil and pyrolysis gasoline.

In the steam cracking process in step (c), the paraffin-containing hydrocarbon feedstock is contacted with steam at a temperature and pressure to form the second effluent which comprises olefins such as ethylene and propylene, including butadiene.

Suitably, the steam cracking process in step (c) is conducted at a temperature from 750 to 920° C., preferably from 760 to 900° C., more preferably from 770 to 890° C., even more preferably 780 to 880° C.; and a pressure of from 1 to 5 bara, preferably from 1.1 to 2.5 bara, more preferably from 1.5 to 2.5 bara.

The paraffin-containing hydrocarbon feedstock to be steam cracked can be chosen from a variety of petroleum fractions. Preferably, the paraffin-containing hydrocarbon feedstock comprises at least one of ethane, propane, butane and/or at least one of a naphtha, kerosene, gasoil or hydrowax.

In step (d), at least part of the first olefinic product fraction as obtained in step (b) and at least part of the second effluent which comprises olefins as obtained in step (c) are combined to form a combined olefinic product stream comprising at least ethylene, propylene and a C4 hydrocarbon fraction comprising butadiene.

Typically, the effluent of a stream cracker is subjected to several treatments upon exiting the steam cracker. For instance, the effluent may first be passed through a primary fractionator to remove heavy hydrocarbon liquids. The remaining effluent may be passed to a quench tower to remove at least a part of the water. Subsequently, the effluent is typically compressed in one or more stages and subjected to an acid gas removal process in an acid gas removal unit and, optionally after further compression, to a drying process in a drying unit. Preferably, the at least part of the first olefinic product fraction as obtained in step (b) and at least part of the second effluent which comprises olefins as obtained in step (c) are combined after second effluent has been subjected to the acid gas removal process. More preferably, the at least part of the first olefinic product fraction as obtained in step (b) and at least part of the second effluent which comprises olefins as obtained in step (c) are combined after second effluent has been subjected to the drying process. The first effluent obtained from the OTO zone will also be subjected to several treatments upon exiting the OTO zone, including catalyst removal, water quench to remove water and an acid gas removal and a drying process, prior to separating the first effluent into the first olefinic product fraction and second olefinic product fraction. Therefore, there is no need to subject the first olefinic product fraction to the same treatment again after combining the first olefinic product fraction with the second effluent. It is, however, possible to separate the first effluent into the first olefinic product fraction and second olefinic product fraction without prior drying. However, this is undesirable due to the risk of hydrate formation/icing in the separation section.

In step (e), at least part of the combined olefinic product stream as obtained in step (d) is subjected to one or more product separation treatments to form at least a product fraction which comprises ethylene and/or propylene and a C4 hydrocarbon product fraction that comprises butadiene. Suitably, the C4 hydrocarbon product fraction that comprises butadiene as obtained in step (e) contains in the range of from 30 to 60 wt % butadiene, based on the total weight of hydrocarbons containing 4 carbon atoms present in the C4 hydrocarbon product fraction that comprises butadiene.

The combined olefinic product stream as obtained in step (d) contains a variety of components, including $C_4+$ components, in addition to ethylene and propylene, which components need to be separated from ethylene and propylene to obtain chemical or polymerization grade ethylene and propylene. The combined olefinic product stream as obtained in step (d) can suitably be passed to one or more fractionation units. In the one or more fractionation units the combined olefinic product stream can be separated into two or more product streams.

Suitably, the combined olefinic product steam is separated into one or more of the following fractions: a $C_5+$ fraction, a $C_4$ fraction, a $C_3$ fraction, a $C_2$ fraction, and a light fraction comprising lighter components such as methane, Hydrogen, carbon oxides and/or inerts. Preferably, the $C_4$ fraction which comprises a mixture of $C_4$ hydrocarbons is subsequently subjected to a butadiene extraction treatment to form a butadiene-enriched $C_4$ product stream and a butadiene-depleted $C_4$ product stream.

Optionally, the butadiene-depleted $C_4$ product stream is combined with the second olefinic product fraction obtained from step (b).

At least part of the butadiene-depleted $C_4$ product stream, or the combined butadiene-depleted $C_4$ product stream and second olefinic product fraction, may be withdrawn from the process as product, such a butadiene-lean $C_4$ product stream is typically referred to as raffinate 1.

Part of the butadiene-depleted product stream so obtained may also be recycled to step (a).

Part of the butadiene-depleted product stream so obtained may also be recycled to step (c), however it is preferred to first fully hydrogenate the olefins in the butadiene-depleted product stream, or the combined butadiene-depleted $C_4$ product stream and second olefinic product fraction, to paraffins. Olefins are less suitable as part of a feedstock to a steam cracking process.

The butadiene extraction treatment can suitably be any butadiene extraction treatment known in the art. For instance, the butadiene extraction treatment can be carried out by extractive distillation using for example acetonitrile, N-methylpyrrolidone, demethylformamide or dimethylacetamide as the solvent. Reference is for instance made to Ullmann's encyclopaedia of Industrial Chemistry, volume 4, VCH, Weinheim, $5^{th}$ edition, 1985, p 347-440 and A. L. Waddams, Chemicals from Petroleum, John Murray, London, $4^{th}$ edition, 1978, p 194-196.

DETAILED DESCRIPTION OF THE DRAWINGS

FIG. 1 shows schematically an embodiment of the present invention.

In FIG. 1, an oxygenate is fed to a reactor 1 via line 2. An olefinic co-feed is fed to the reactor as well, via line 3. In the reactor system 1, the oxygenate and the olefinic co-feed are allowed to react in the presence of a phosphorus and ZSM 5 comprising catalyst to form a first effluent which comprises olefins. The first effluent is passed via line 4 to a separation section 5 to form a first olefinic product fraction comprising at least ethylene and propylene and a third olefinic product fraction which comprises olefins containing 4 carbon atoms and a fourth olefinic product fraction which comprises olefins containing 5 or more carbon atoms. The first olefinic product fraction is recovered in line 6 and the third olefinic product fraction is recovered in line 7 and the fourth olefinic product fraction is recovered in line 8. At least part of the third olefinic product stream is recycled to the reactor 1, while part of the third olefinic product stream is purged via line 7a. At least part of the fourth olefinic product stream is provided to OCP reaction zone 9, the effluent of which is recycled via line 10 to separation section 5. A paraffin-containing hydrocarbon feedstock is fed to a reactor 11 via line 12. In reactor 11, the paraffin-containing hydrocarbon feedstock is steam cracked to form a second effluent which comprises olefins including butadiene. At least part of the second effluent is passed together with the first olefinic product stream as obtained in line 6 via line 13 to a fractionation section 14, optionally after the second effluent has been subjected to one or more treatments to remove for instance liquid hydrocarbons, water and acid gases (not shown). In this embodiment the separation section is shown to produce an ethylene-rich product stream in line 15, propylene-rich product stream in line 16, a $C_4$ fraction in line 17, a $C_5$+ hydrocarbon rich stream in line 18, and a light fraction in overhead line 19 comprising lighter components such as methane, hydrogen, carbon oxides and/or inerts. The $C_4$ fraction so obtained is passed via line 17 to a butadiene extraction unit 25 to form a butadiene-enriched product stream which is recovered via line 30 and a butadiene-depleted product stream which is recycled to reactor 1 via line 35, while part of the butadiene-depleted product stream is purged via line 35a.

The $C_5$+ hydrocarbon rich stream in line 18 may be combined with the fourth olefinic product fraction in line 8 and provided to OCP reaction zone 9.

Example

The invention is illustrated by the following non-limiting example.

To show the advantageous effect of the process according to the present invention the impact on the butadiene extraction unit is calculated for an integration of a methanol to olefins process using a methanol feedstock with a steam cracking process, wherein the latter uses a liquid naphtha feedstock. The methanol to olefins process produces a first effluent in a process as defined in step (a) of the invention. The steam cracking process produces a second effluent in a process as defined in step (c) of the invention. Both the first and the second effluent will comprise ethylene, propylene and a C4 hydrocarbon fraction. Table 1, provides a model composition of the C4 hydrocarbon fraction of both the first and second effluent similar to the composition that would be obtained from a real process.

TABLE 1

|  | First effluent (MTO) | | Second effluent (SC) | |
| --- | --- | --- | --- | --- |
|  | Flows, t/h | Wt % | Flows, t/h | Wt % |
| Butadiene | 0 | 0 | 13.0 | 47.1 |
| Butenes | 18.0 | 67.7 | 11.5 | 41.7 |
| Butanes | 8.6 | 32.3 | 3.1 | 11.2 |
| Total | 26.6 | | 27.6 | |

The methanol to olefins process and steam cracker process are integrated by combining at least part of first and second effluent, subsequently the combined effluent is fractionated to recover the ethylene and propylene and a separate C4 hydrocarbon fraction.

Two integration schemes were modelled:

Scheme A—a scheme according to the invention, wherein the C4+ hydrocarbon fraction of the first effluent is separated from the first effluent prior to combining the remainder of first effluent, i.e. the first olefinic product according to the invention comprising ethylene and propylene, with the second effluent and the C4 hydrocarbon fraction of the combined effluent (i.e. combined olefinic product stream according to the invention) is provided to the butadiene extraction unit.

Scheme B—a scheme not according to the invention, wherein the first effluent is combined with the second effluent and the C4 hydrocarbon fraction of the combined effluent is provided to the butadiene extraction unit;

Table 2, provides the composition of the C4 hydrocarbon fraction of the combined effluent obtained via scheme A and scheme B.

Subsequently, the butadiene is separated from the C4 hydrocarbon fraction of the combined effluent by providing the C4 hydrocarbon fraction of the combined effluent to a butadiene extraction unit. A typical butadiene extraction unit contains as major equipment units an extractive distillation column and a stripper section. The butadiene is separated from the rest of the C4 hydrocarbons by using solvents such as acetonitrile. The butadiene is extracted with the solvent in the extractive distillation column, where after the butadiene is stripped from the loaded solvent in the stripper section In a typical acetonitrile based butadiene extraction unit the circulation rate of acetonitrile is approximately 7.5 times the C4s feed rate on a weight basis.

TABLE 2

| | Composition of C4 hydrocarbon fraction | | | |
| --- | --- | --- | --- | --- |
| | Scheme A | | | |
| | Flows, t/h | Wt % | Flows, t/h | Wt % |
| Butadiene | 13.0 | 47.1 | 13.0 | 24.0 |
| Butenes | 11.5 | 41.7 | 29.5 | 54.4 |
| Butanes | 3.1 | 11.2 | 11.7 | 21.6 |
| Total | 27.6 | | 54.2 | |

Based on the size of the C4 hydrocarbon fractions provided in Table 2, this would result in an acetonitrile circulation rate of 207 t/h for scheme A, i.e. according to the invention, compared to a the prior art scheme B, that would required an acetonitrile circulation rate of 406 t/h.

It will be clear from the calculations above the process according to the invention provides a significant improvement of the efficiency of the butadiene extraction. The process according to the invention allows for a 49% reduction of the acetonitrile circulation on a weight basis. Typically, this will effect a reduction of the CAPEX by roughly 30% and lower the OPEX by roughly 50%.

That which is claimed is:

1. An integrated process for the preparation of olefins, which process comprises the steps of:
   (a) reacting an oxygenate feed in a first reactor in the presence of a molecular sieve catalyst to form a first effluent which comprises olefins;
   (b) fractionating at least part of the first effluent into a first olefinic product fraction comprising at least ethylene and propylene and a second olefinic product fraction which comprises olefins containing 4 or more carbon atoms;
   (c) subjecting a paraffin-containing hydrocarbon feedstock in a second reactor to a steam cracking process to form a second effluent which comprises olefins, including butadiene;
   (d) combining at least part of the first olefinic product fraction as obtained in step (b) and at least part of the second effluent which comprises olefins as obtained in step (c) to form a combined olefinic product stream comprising at least ethylene, propylene and a C4 hydrocarbon fraction comprising butadiene; and
   (e) subjecting at least part of the combined olefinic product stream as obtained in step (d) to one or more product separation treatments to form at least a product fraction which comprises ethylene and/or propylene and a C4 hydrocarbon product fraction that comprises butadiene wherein the first effluent as obtained in step (a) comprises less than 6.0 wt % butadiene, based on the total weight of hydrocarbons containing 4 carbon atoms present in the first effluent.

2. The process according to claim 1, wherein step (b) is carried out by passing the first effluent to separation section comprising a depropaniser unit and the first olefinic product fraction is retrieved as the top fraction of the depropaniser unit.

3. The process according to claim 1, wherein at least part of the second olefinic product fraction is recycled to step (a).

4. The process according to claim 1, wherein at least part of the second olefinic product fraction is provided to an olefin cracking process.

5. The process according to claim 1, wherein the C4 hydrocarbon product fraction that comprises butadiene as obtained in step (e) is subjected to a butadiene extraction treatment to form a butadiene-enriched product stream and butadiene-depleted product stream.

6. The process according to claim 1, wherein the C4 hydrocarbon product fraction that comprises butadiene as obtained in step (e) contains in the range of from 30 to 60 wt % butadiene, based on the total weight of hydrocarbons containing 4 carbon atoms present in the product fraction that comprises butadiene.

7. The process according to claim 1, wherein the molecular sieve catalyst in step (a) comprises a MFI or MEL zeolite.

8. The process according to claim 1, wherein the oxygenate feed in step (a) comprises methanol and/or dimethylether.

9. The process according to claim 1, wherein the paraffin-containing hydrocarbon feedstock comprises at least one of ethane, propane, butane and/or at least one of a naphtha, kerosene, gasoil or hydrowax.

10. The process according to claim 1, wherein the reaction in step (a) is conducted at a temperature from 350 to 750° C. Previously.

11. The process according to claim 1, wherein the steam cracking process in step (c) is conducted at a temperature from 750 to 920° C.

12. The process according to claim 1, wherein the first effluent as obtained in step (a) comprises less than 5.0 wt % butadiene, based on the total weight of hydrocarbons containing 4 carbon atoms present in the first effluent.

* * * * *